United States Patent [19]

Lantzsch et al.

[11] Patent Number: 4,686,291
[45] Date of Patent: Aug. 11, 1987

[54] PREPARATION OF METHYL KETONES

[75] Inventors: Reinhard Lantzsch, Leverkusen; Hans-Ludwig Elbe, Wuppertal, both of Fed. Rep. of Germany

[73] Assignee: Bayer Aktiengesellschaft, Leverkusen, Fed. Rep. of Germany

[21] Appl. No.: 802,076

[22] Filed: Nov. 26, 1985

Related U.S. Application Data

[63] Continuation of Ser. No. 475,011, Mar. 14, 1983, abandoned.

[30] Foreign Application Priority Data

Mar. 24, 1982 [DE] Fed. Rep. of Germany ....... 3210725

[51] Int. Cl.⁴ .................... C07C 45/61; C07D 239/26; C07D 213/46; C07D 333/06
[52] U.S. Cl. .................................. 544/335; 546/340; 549/78; 549/498; 568/393; 568/348
[58] Field of Search ................ 568/393, 348; 546/340; 549/78, 498; 544/335

[56] References Cited

FOREIGN PATENT DOCUMENTS 1029064 12/1950 France ................................ 568/393

OTHER PUBLICATIONS

Translation from Zhurnal Organicheskoi Khimii, vol. 17, No. 2, pp. 329–332, Feb. 1981, "Alkylation of Carbonyl Compounds . . .", pp. 277–279.
Advanced Organic Chemistry, Mc-Graw-Hill Book Company, N.Y., Second Edition, pp. 160–161 and pp. 418–420.
Eastman Organic Chemical Bulletin, vol. 48, No. 1, pp. 1–3, (1976).
Brandstrom et al., Chem. Abstracts, vol. 76, No. 15, Abst. No. 84949w, Apr. 10, 1972.
Brandstrom et al., Chem. Abstracts, vol. 72, No. 17, Abst. No. 89702n, Apr. 27, 1970.

*Primary Examiner*—Alan L. Rotman
*Attorney, Agent, or Firm*—Sprung Horn Kramer & Woods

[57] ABSTRACT

A process for the preparation of a methyl ketone of the formula

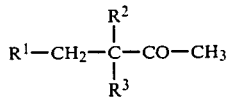

in which
$R^1$ is alkyl, alkenyl, alkinyl, optionally substituted aryl or optionally substituted heteroaryl,
$R^2$ is alkyl,
$R^3$ is alkyl or
$R^2$ and $R^3$, together with the carbon atom to which they are bonded, from a cycloalkyl ring, comprising reacting a methyl sec.-alkyl ketone of the formula

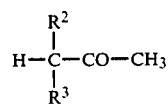

with a halide of the formula

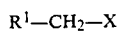

in which
X is halogen, in the presence of a base, a diluent, and a phase-transfer catalyst.

6 Claims, No Drawings

PREPARATION OF METHYL KETONES

This application is a continuation of application Ser. No. 475,011, filed Mar. 14, 1983.

The present invention relates to a new, advantageous process for the preparation of methyl ketones, some of which are known, and which can be used as intermediate products for the synthesis of plant protection agents.

It has already been disclosed that ketones and aldehydes can be alkylated under conditions of phase-transfer catalysis. In this process, however, aldehydes are permitted to contain a hydrogen atom only in the α-position, since otherwise the yields fall to below 20% as a result of dialkylation and O-alkylation (see Chemistry and Industry, 1978, 732). Ketones give good yields of the desired monoalkylation product only when additional activation by an aryl radical, such as, for example, in phenylacetone ($C_6H_5$—$CH_2$—$CO$—$CH_3$), is present. In other cases, such as, for example, in the case of acetophenone or acetone, mixtures of mono-, di- and O-alkylated products are formed, the yields of the monoalkylated product being low (see Tetrahedron Letters 18, 1351-52 (1971) and Journal of Organic Chemistry of the USSR 17, 329 (1981)).

It has been found that the methyl ketones, some of which are known, of the general formula

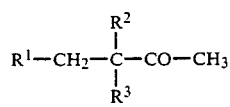
                                        (I)

in which
R$^1$ represents alkenyl, alkinyl, optionally substituted aryl or optionally substituted heteroaryl,
R$^2$ represents alkyl,
R$^3$ represents alkyl, or
R$^2$ and R$^3$, together with the carbon atom to which they are bonded, represent cycloalkyl, are advantageously obtained in good yields when methyl sec.-alkyl ketones of the formula

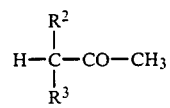
                                        (II)

in which
R$^2$ and R$^3$ have the meanings given above, are reacted with halides of the formula $$R^1—CH_2—X \quad (III)$$

in which
R$^1$ has the meaning given above and
X represents halogen, in the presence of a base and of a diluent, and in the presence of a phase-transfer catalyst.

In view of the prior art, it is surprising that the reaction according to the invention proceeds in the desired manner, and no di-, tri-, tetra- or O-alkylation occurs and no secondary reactions and condensations of the methyl sec.-alkyl ketones of the formula (II) with themselves are to be observed.

The process according to the invention gives the methyl ketones of the formula (I) in an advantageous manner, in very good yields.

Formula (I) gives a general definition of the methyl ketones obtainable by the process according to the invention. In this formula,
R$^1$ preferably represents straight-chain or branched alkyl having 1 to 6 carbon atoms, alkenyl having 2 to 6 carbon atoms and alkinyl having 2 to 4 carbon atoms, and also represents optionally substituted phenyl, the following being mentioned as substituents: halogen, alkyl having 1 to 4 carbons atoms, alkoxy and alkylthio, each having 1 to 2 carbon atoms, as well as halogenoalkyl, halogenoalkoxy and halogenoalkylthio, each having 1 to 2 carbon atoms and 1 to 5 identical or different halogen atoms, such as, preferably, fluorine atoms and chlorine atoms, and dialkylamino having 1 to 4 carbon atoms in each alkyl part; or also represents 5-membered or 6-membered heteroaryl which has 1 to 2 hetero atoms, such as, preferably, nitrogen atoms, oxygen atoms and sulphur atoms, and which is optionally substituted by alkyl having 1 to 2 carbon atoms and/or by halogen;
R$^2$ preferably represents straight-chain or branched alkyl having 1 to 4 carbon atoms; R$^3$ preferably represents straight-chain or branched alkyl having 1 to 4 carbon atoms or R$^2$ and R$^3$, together with the carbon atoms to which they are bonded, preferably represent cycloalkyl having 3 to 6 carbons atoms.

Particularly preferred methyl ketones of the formula (I) are those
in which
R$^1$ represents straight-chain or branched alkyl having 1 to 4 carbon atoms, alkenyl having 2 to 4 carbon atoms and alkinyl having 2 to 4 carbon atoms; and also represents optionally substituted phenyl, the following being mentioned as substituents: fluorine, chlorine, bromine, methyl, ethyl, isopropyl, tert.-butyl, methoxy, methylthio, trifluoromethyl, trifluoromethoxy, trifluoromethylthio, dimethylamino and ethylmethylamino; and also represents pyrimidinyl, furyl, thiophenyl or pyridyl which is optionally substituted by fluorine, chlorine, bromine, methyl and/or ethyl;
R$^2$ represents methyl;
R$^3$ represents methyl, or
R$_2$ and R$_3$, together with the carbon atom to which they are bonded, represent cyclopropyl.

If, for example, isopropyl methyl ketone and 4-chlorobenzyl chloride are used as starting materials, the course of the reaction of the process according to the invention can be represented by the following equation:

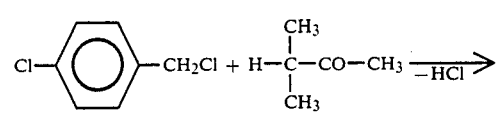

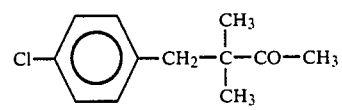

Formula (II) gives a general definition of the methyl sec.-alkyl ketones to be used as starting materials for the process according to the invention. In this formula, $R^2$ and $R^3$ preferably represents the radicals which have already been mentioned in the description of the substances which can be prepared according to the invention, of the formula (I), as being preferred for these substituents.

The methyl sec.-alkyl ketones of the formula (II) are generally known compounds of organic chemistry.

Formula (III) gives a general definition of the halides additionally to be used as starting materials for the process according to the invention. In this formula, $R^1$ preferably represents the radicals which have already been mentioned in the description of the substances which can be prepared according to the invention, of the formula (I), as being preferred for these substituents. X preferably represents chlorine.

The halides of the (III) are likewise generally known compounds of organic chemistry.

Preferred diluents for the reaction according to the invention are inert organic solvents which are stable to bases. These solvents preferably include (cyclo)aliphatic and optionally chlorinated aromatic hydrocarbons, such as benzene, xylene, chlorobenzene, dichlorobenzene, cyclohexane, petroleum ether, benzine, pentane, hexane and in particular toluene.

Preferred bases for the reaction according to the invention are alkali metal hydroxides and alkaline earth metal hydroxides, such as, in particular, powdered potassium hydroxide and sodium hydroxide. Technical grade potassium hydroxide is preferably employed.

All customarily usable derivatives of ammonium salts, such as, for example, triethylbenzylammonium chloride, tetrabutylammonium iodide and in particular tetrabutylammonium bromide or tetrabutylammonium chloride and trioctylmethylammonium chloride, can be employed as phase-transfer catalysts.

In the reaction according to the invention, the reaction temperatures can be varied within a relatively wide range. In general, the reaction is carried out at between 0° and 150° C., preferably between +20 and 130° C.

In carrying out the reaction according to the invention, 1 mol of halide of the formula (III) and catalytic amounts of the catalysts are preferably employed per 1 or 2 mols of the ketone of the formula (II). In a preferred form of carrying out the reaction, the catalyst and the base in the solvent are initially introduced, and the halide of the formula (III) as a mixture with the ketone of the formula (II) is slowly added dropwise at the reaction temperature. Some of the methyl ketones which can be prepared according to the invention, of the formula (I), are known (see, for example, Bull. Soc. Chim. France 1970, 912 or C.R. Séances Acad. Sci., Ser. C 269 (1969) 18, 1052–1055); they can be employed as intermediate products for the preparation of fungicidal, insecticidal, herbicidal and/or plant growth-regulating compounds.

For example, fungicidally active compounds of the formula (IV) are obtained from methyl ketones of the formula (Ia), according the the following equation (see U.S. application, Ser. No. 328,871, filed Dec. 8, 1981, now pending):

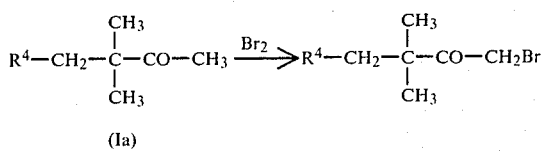

(Ia)

$R^4$=optionally substituted phenyl

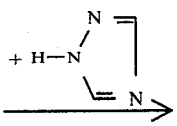

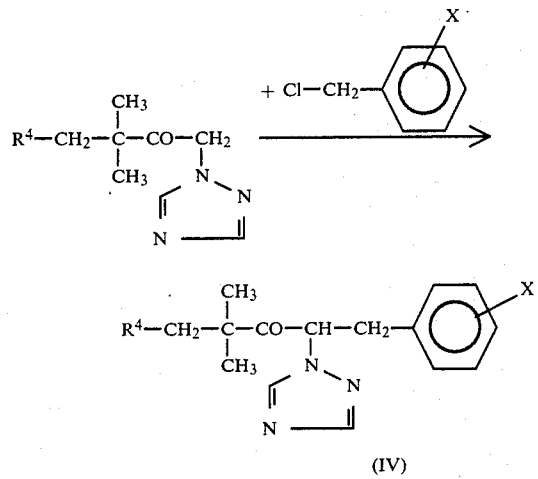

(IV)

X=for example, hydrogen or halogen

PREPARATION EXAMPLES

EXAMPLE 1

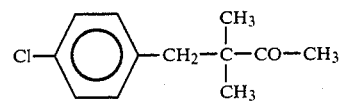

254.4 g (4 mols) of powdered technical grade potassium hydroxide (88% strength) are suspended in 1 liter of toluene, 40 g of tetrabutylammonium bromide are added, and a mixture of 644 g (4 mols) of 4-chlorobenzyl chloride and 430 g (5 mols) of methyl isopropyl ketone is then slowly added dropwise at 85° C. To complete the reaction, the mixture is stirred for a further 3 hours at 85° C. after the dropwise addition is complete. After the mixture has been cooled, the potassium chloride is filtered off and the filtrate is washed neutral. 732.5 g (87% of theory) of 1-(4-chlorophenyl)-2,2-dimethylbutan-3-one of boiling point 87°–90° C./0.05 mbar are obtained by fractional distillation.

EXAMPLE 2

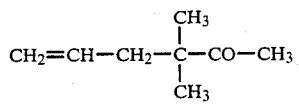

63.6 g (1 mol) of powdered potassium hydroxide (88% strength) are metered into a mixture of 250 ml of toluene, 86 g (1 mol) of methyl isopropyl ketone, 69 g (0.9 mol) of allyl chloride and 10 g of tetrabutylammonium bromide. The reaction is exothermic. After the addition is complete, the mixture is stirred for a further 12 hours at 100° C. The mixture is worked up according to Example 1, and 77 g (67.9% of theory) of 4,4-dimethylhex-1-en-5-one of boiling point 45°–46° C./12 mbar are obtained, or 63.6 g (1 mol) of powdered technical grade potassium hydroxide (88% strength) are suspended in 200 ml of toluene, and 10 g of trioctylammonium chloride are added. A mixture of 76.5 g (1 mol) of allyl chloride and 129 g (1.5 mols) of methyl isopropyl ketone is then added dropwise so that the temperature does not exceed 70° C. The mixture is stirred for a further 4 hours at 70° C., and is worked up as in Example 1. 96 g (76% of theory) of 4,4-dimethylhex-1-en-5-one of the abovementioned boiling point are obtained.

EXAMPLE 3

$$HC\equiv C-CH_2-\underset{\underset{CH_3}{|}}{\overset{\overset{CH_3}{|}}{C}}-CO-CH_3$$

70 g (1.1 mols) of powdered technical grade potassium hydroxide (88% strength) and 10 g of tetrabutylammonium bromide in 250 ml of toluene are initially introduced. A mixture if 119 g (1 mol) of propargyl bromide and 103.2 g (1.2 mols) of methyl isopropyl ketone is then added dropwise so that the temperature does not exceed 45° C. The mixture is stirred for a further 12 hours at 45° C., and is worked up according to Example 1. 67 g (54% of theory) of 4,4-dimethyl-hex-1-in-5-one of boiling point 55° C./12 mbar are obtained.

EXAMPLE 4

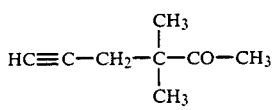

516 g (6 mols) of methyl isopropyl ketone, 759 g (6 mols) of benzyl chloride and 60 g (0.186 mol) of tetrabutylammonium bromide are dissolved in 1 liter of toluene, and the solution is heated to 100° C. 420 g (7.49 mols) of powered potassium hydroxide are slowly metered in at this temperature. The reaction mixture is stirred for 12 hours at 100° C. and cooled, and 1.5 liters of water are added. The organic phase is separated off, dried over sodium sulphate and distilled fractionally. 507 g of 3,3-dimethyl-4-phenylbutan-2-one of boiling point 82° C./0.05 mbar are obtained.

The following compounds of the general formula (I)

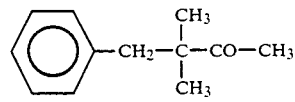

can be obtained in a corresponding manner:

| Example No. | $R^1$ | $R^2$ | $R^3$ | Physical constant |
|---|---|---|---|---|
| 5 | 2,3-dichlorophenyl | $CH_3$ | $CH_3$ | Bp: 90–95° C./ 0.06 mbar |
| 6 | 4-(trifluoromethoxy)phenyl | $CH_3$ | $CH_3$ | Bp: 56° C./ 0.05 mbar |
| 7 | 2-pyridyl | $CH_3$ | $CH_3$ | Bp: 75–80° C./ 0.05 mbar |
| 8 | 3-methyl-2-thienyl | $CH_3$ | $CH_3$ | Bp: 66–70° C./ 0.15 mbar |
| 9 | $C_2H_5$ | $CH_3$ | $CH_3$ | Bp: 140–46° C. |
| 10 | $n-C_3H_7$ | $CH_3$ | $CH_3$ | Bp: 59–65° C./ 18 mbar |
| 11 | $CH_3-CH=CH-$ | $CH_3$ | $CH_3$ | Bp: 66–71° C./ 28 mbar |
| 12 | 2-chlorophenyl | $CH_3$ | $CH_3$ | Bp: 70–75° C./ 0.05 mbar |
| 13 | 2,3-dichlorophenyl | $CH_3$ | $CH_3$ | Bp: 110–15° C./ 0.1 mbar |
| 14 | 4-methylphenyl | $CH_3$ | $CH_3$ | Bp: 72–77° C./ 0.05 mbar |
| 15 | 2,6-dichlorophenyl | $CH_3$ | $CH_3$ | Bp: 100–0.5° C./ 0.1 mbar |
| 16 | 3-methylphenyl | $CH_3$ | $CH_3$ | Bp: 87° C. 0.4 mbar |
| 17 | 4-fluorophenyl | $CH_3$ | $CH_3$ | Bp: 67–70° C. 0.05 mbar |

PREPARATION OF THE SECONDARY PRODUCT

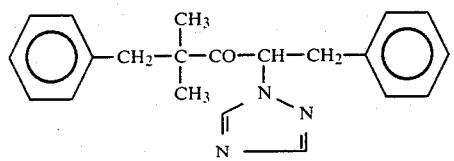 (a)

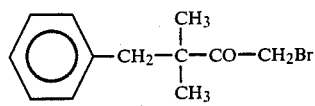

100 g (0.57 mol) of 3,3-dimethyl-4-phenylbutan-2-one (Example 5) are dissolved in 0.8 liter of chloroform, and 29 ml (91.9 g; 1.14 mols) of bromine are added slowly at room temperature. The mixture is stirred for a further hour at room temperature and is concentrated. 145.5 g (quantitative) of 1-bromo-3,3-dimethyl-4-phenylbutan-2-one are obtained, and this directly reacted further, without isolation.

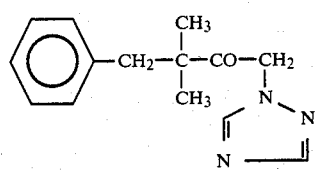 (b)

74 g (0.29 mol) of 1-bromo-3,3-dimethyl-4-phenylbutan-2-one, 40 g (0.58 mol) of 1,2,4-triazole and 80 g of potassium carbonate are dissolved in 700 ml of acetone, and the solution is heated under reflux for 3 hours. Thereafter, it is allowed to cool and is filtered off under suction from the inorganic residue, and the filtrate is concentrated. The residue is recrystallized from ether. 34.1 g (48.4% of theory) of 3,3-dimethyl-4-phenyl-1-(1,2,4-triazol-1-yl)-butan-2-one of melting point 79° C. are obtained.

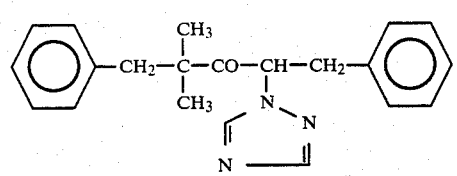 (c)

48.6 g (0.2 mol) of 3,3-dimethyl-4-phenyl-1-(1,2,4-triazol-1-yl)-butan-2-one, 27.9 g (0.22 mol) of benzyl chloride and 12.3 g (0.22 mol) of potassium hydroxide in 15 ml of water are dissolved in 300 ml of dimethylsulphoxide. The reaction mixture is stirred for a further 8 hours at 50° C. and then poured onto water. The mixture is extracted with ethyl acetate. The organic phase is concentrated and the residue is purified by column chromatography (silica gel/ethyl acetate: cyclohexane =3:1). 54.5 g (81.8% of theory) of 1,5-bisphenyl-2,2-dimethyl-4-(1,2,4-triazol-1-yl)-pentan-3-one of melting point 45°–50° C. are obtained.

It will be understood that the specification and examples are illustrative but not limitative of the present invention and that other embodiments within the spirit and scope of the invention will suggest themselves to those skilled in the art.

What is claimed is:

1. A process for the preparation of a methyl ketone of the formula

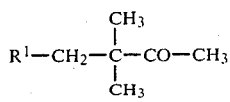

in which
R$^1$ is alkyl, having 1 to 6 carbon atoms, alkenyl having 2 to 6 carbon atoms, alkinyl having 2 to 4 carbon atoms, phenyl optionally substituted by halogen, alkyl having 1 to 4 carbon atoms, alkoxy or alkylthio, each having 1 to 2 carbon atoms, as well as halogenoalkyl, halogenoalkoxy and halogenoalkylthio, each having 1 to 2 carbon atoms or 1 to 5 identical or different halogen atoms, or dialkylamino having 1 to 4 carbon atoms in each alkyl part; or also R$^1$ represents 5-membered or 6-membered heteroaryl selected from the group consisting of pyridal, pyrimidinyl, furyl or thienyl, wherein each heteroaryl is unsubstituted or optionally substituted by alkyl having 1 to 2 carbon atoms or by halogen, comprising reacting at a temperature between about 0° and 150° C. a methyl sec.-alkyl ketone of the formula

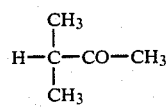

with a halide of the formula

in which
X is halogen,
in the presence of a base, a diluent, and a phase-transfer catalyst.

2. A process according to claim 1, wherein the reaction is carried out at a temperature between about +20° and 130° C.

3. A process according to claim 1, wherein the base is an alkali metal hydroxide or alkaline earth metal hydroxide.

4. A process according to claim 1, wherein the phase transfer catalyst is an ammonium salt.

5. A process according to claim 3, wherein the base is an alkali metal hydroxide or alkaline earth metal hydroxide, and the phase transfer catalyst is an ammonium salt.

6. A process according to claim 1, in which R$^1$ is alkyl having 1 to 4 carbon atoms; alkenyl having 2 to 4 carbon atoms; alkinyl having 2 to 4 carbon atoms; phenyl optionally substituted by fluorine, chlorine, bromine, methyl, ethyl, isopropyl, tert.-butyl, methoxy, methylthio, trifluoromethyl, trifluoromethoxy, trifluoromethylthio, dimethylamino or ethylmethylamino; or R$^1$ represents pyrimidinyl, furyl, thienyl or pyridyl rings unsubstituted or optionally substituted by fluorine, chlorine, bromine, methyl or ethyl.

* * * * *

UNITED STATES PATENT AND TRADEMARK OFFICE
CERTIFICATE OF CORRECTION

PATENT NO. : 4,686,291

DATED : August 11, 1987

INVENTOR(S) : Reinhard Lantzsch, et al.

It is certified that error appears in the above-identified patent and that said Letters Patent is hereby corrected as shown below:

| | |
|---|---|
| Col. 1, line 37 | Before "alkenyl" insert --alkyl,-- |
| Col. 1, line 61 | Correct spelling of --diluent-- |
| Col. 2, line 30 | Delete "carbons" and substitute --carbon-- |
| Col. 3, line 2 | Delete "represents" and substitute --represent-- |
| Col. 3, line 19 | Before "(III)" insert --formula-- |
| Col. 3, line 68 | Delete "now pending" and substitute --abandoned-- |
| Col. 7, line 1 | Delete "THE" and substitute --A-- |
| Col. 8, line 25 | Delete "pyridal" and substitute --pyridyl-- |
| Col. 8, line 53 | Delete "claim 3" and substitute --claim 2-- |

Signed and Sealed this

Tenth Day of May, 1988

Attest:

DONALD J. QUIGG

Attesting Officer

Commissioner of Patents and Trademarks